United States Patent [19]

Nagashima

[11] Patent Number: 5,640,236
[45] Date of Patent: Jun. 17, 1997

[54] METHOD AND APPARATUS FOR DETECTING THE POSITION OF DEFECT IN A HOLLOW FIBER MEMBRANE MODULE

[75] Inventor: Hideyuki Nagashima, Fujisawa, Japan

[73] Assignee: NOK Corporation, Tokyo, Japan

[21] Appl. No.: 378,826

[22] Filed: Jan. 27, 1995

Related U.S. Application Data

[62] Division of Ser. No. 144,019, Nov. 1, 1993, Pat. No. 5,411,682.

[30] Foreign Application Priority Data

Oct. 30, 1992 [JP] Japan ................................ 4-316480

[51] Int. Cl.$^6$ .................................................. B01D 65/10
[52] U.S. Cl. ........................... 356/237; 73/40.7; 264/40.1
[58] Field of Search ................................. 356/237, 337, 356/338, 343; 73/37, 40.7; 264/36, 40.1

[56] References Cited

U.S. PATENT DOCUMENTS

| | | | |
|---|---|---|---|
| 4,188,117 | 2/1980 | Yamauchi et al. | 356/237 |
| 4,188,817 | 2/1980 | Steigelmann | 73/40.7 |
| 4,875,360 | 10/1989 | Ziemer | 73/40.7 |

FOREIGN PATENT DOCUMENTS

| | | |
|---|---|---|
| 2 389 116 | 11/1978 | France . |
| 2 671 184 | 7/1992 | France . |
| 53-134776 | 11/1978 | Japan . |
| 54-138874 | 10/1979 | Japan . |
| 2-14084 | 4/1990 | Japan . |
| 3-169329 | 7/1991 | Japan . |

OTHER PUBLICATIONS

Database WPI, Week 7949, Oct. 21, 1979, Derwent Publications ltd., JP-A-54-138-874 (Kuraray KK), Apr. 20, 1978.

Patent Abstracts of Japan, vol. 17, No. 606 (C-1128), Nov. 8, 1993, JP-A-5-184-886 IKuraray Co., Ltd.), Jul. 27,1 993.

Patent Abstracts of Japan, vol. 15, No. 421 (C-0878), Oct. 25, 1991, JP-A-03-174-225 (Mitsubishi Rayon Co., Ltd.), Jul. 29, 1991.

Patent Abstract of Japan, vol. 15, No. 421 (C-0878), oct. 24, 1991, JP-A-03-174-226 (Mitsubishi Tayon Co., Ltd.), Jul. 29, 1991.

*Primary Examiner*—Richard A. Rosenberger
*Attorney, Agent, or Firm*—Jacobson, Price, Holman & Stern, PLLC

[57] ABSTRACT

A method and apparatus for detecting, with a high degree of reliability and precision, a two dimensional position of any defects that might be present in a microporous hollow fiber membrane module (10) as manufactured. Detection of defects is carried out in a dark chamber (42) in which the module (10) to be tested is placed. Air carrying fine airborne particles having a particle size larger than the pore size of the micropores of the hollow fibers is forced to flow through the module. A laser beam (54) is projected closely adjacent to the end face (22) of the module to irradiate any particles that have passed the defects. Upon irradiation, the microscopic particles scatter the incident beam and are visualized by scattered light. The light intensity of the visualized scene of particles is magnified by an image intensifier (64) and a video camera (68) generates video signals of the intensified image. The video signals are processed by an image processor (70) which computes and identifies the two dimensional position of the defects.

5 Claims, 5 Drawing Sheets

METHOD AND APPARATUS FOR DETECTING THE POSITION OF DEFECT IN A HOLLOW FIBER MEMBRANE MODULE

This is a divisional of application Ser. No. 08/144,019 filed Nov. 1, 1993, now U.S. Pat. No. 5,411,682.

BACKGROUND OF THE INVENTION

1. Field of the Invention

The present invention relates to a method and apparatus for testing a microporous hollow fiber membrane module for the presence or absence of a defect. More particularly, this invention is directed to a method and apparatus wherein, in the presence of any defect, the two dimensional position thereof is detected to enable proper repair and mending.

2. Description of the Prior Art

Hollow fiber membrane modules are widely used for various purposes such as filtration of aqueous or gaseous fluid, ultrafiltration of particulate materials and dialysis of blood. Generally, a hollow fiber membrane module includes a bundle of microporous hollow fibers arranged in a tubular casing, as illustrated, for example, in Japanese Patent Kokoku Publication No. 2-14084. In one form, the fiber bundle is bent into the U-shape with the ends of respective fibers supported by a partition wall of potting resin bonded to the casing. The potting resin forming the partition wall serves to sealingly fill the interstices between fibers, with the inner channels of respective fibers being open onto the outer face of the partition wall. In another form, the straight fibers are used with their opposite ends bonded to separate partition walls.

Defect may occasionally be present for various reasons in the hollow fiber membrane modules as fabricated. For instance, during extrusion spinning of the hollow fibers, pinholes or fissure may inadvertently be formed in the microporous membrane forming the hollow fibers. Furthermore, the hollow fibers may be damaged during subsequent handling. In addition, voids and cavities formed across the partition wall during molding of potting resin as well as shortage of bonding between fibers and potting resin may result in short-paths of fluid circumventing the micropores of the hollow fibers.

Japanese Patent Kokoku Publication No. 2-14084 discloses a method of testing a hollow fiber membrane module for a defect wherein air carrying fine airborne particles is drawn across the module and is forwarded to a particle counter for counting the number of particles that have passed the module. The sensitivity of the particle counter is adjusted to count only those particles having a size larger than a predetermined level. If any particles are counted, it is judged that the module is defective.

While this method permits inspection of the modules for the presence or absence of a defect, repair of defective modules is impossible because the specific position of defect is not identified. Therefore, the defective modules must be discarded as a whole without repair even though only a single fiber is defective. This lowers the production yield and leads to a waste of materials and resources.

Japanese Patent Kokai Publication No. 53-134776 describes a method of detecting the position of a defective portion of a hollow fiber membrane module. The method includes supplying a pressurized gas to the unfiltered side of the module to cause the gas to leak through the defect. The rate of gas leakage through a defective portion will be higher than the flow rate across non-defective fibers so that a refraction anomaly is resulted at the defective portion. This refraction anomaly is visualized by an optical system according to the schlieren method and the location of the defective portion is identified. Once the position of the defect is determined, an adhesive may be applied to seal the defective portion as disclosed in Japanese Patent Kokai Publication No. 54-138874.

According to this method, however, it is often difficult to distinguish the refraction anomalies with reliability because, due to the fluctuation in the flow resistance through respective hollow fibers, the velocity of gas flowing out of the inner channels of respective fibers varies considerably from fiber to fiber. Moreover, it is extremely difficult to find out the refraction anomalies resulting from microscopic defects which are of a size in the order of micrometers or less and which would nevertheless affect the quality of the module.

SUMMARY OF THE INVENTION

Accordingly, an object of the present invention is to provide an improved method and apparatus for testing a hollow fiber membrane module for the presence or absence of a defect and for detecting, in the presence of a defect, a two dimensional position thereof.

Another object of the invention is to provide a method and apparatus wherein the two dimensional position of a defect is identified with a high degree of reliability and precision.

A still another object of the invention is to provide a method and apparatus wherein determination of the two dimensional position of a defect is readily carried out.

A further object of the invention is to provide a method and apparatus which is capable of detecting and identifying microscopic defects in order to provide a hollow fiber membrane module of a high quality.

According to the method and apparatus of the invention, the module to be tested is positioned within a substantially dust-free, preferably dark enclosure. A gaseous fluid carrying fine particles of light scattering material having a particle size larger than the effective pore size of the micropores of the hollow fibers is forced to flow through the module from the unfiltered to filtered sides thereof. Preferably, the size of the particles is in the order of a fraction of a micrometer in order to achieve detection of submicron defects. To this end, sized fine particles of polystyrene may be used. Alternatively, ambient air carrying airborne dusts may well be used. If any defects larger in size than the micropores of the membrane are present, the airborne particles or dusts will be brought to the filtered side of the module.

While the gaseous fluid or air is forced to flow across the module, light rays are projected by an optical system along a plane parallel to and closely adjacent to the end face of the partition wall of the module to irradiate any particles that have passed any defects in the module. Projection of light rays may be made either by constantly projecting light rays in the form of slit-light or by cyclically scanning a beam over the end face. Preferably, a laser beam is used to provide scattered light rays of high intensity.

Upon irradiation, the microscopically fine particles or dusts which are ordinarily invisible to the eyes will scatter light rays and, therefore, are visualized. The scene of the scattered light rays is rather instantaneous in nature since the moving airborne particles will rapidly traverse the plane of projected light rays. However, by visually observing the scene of the scattered light rays on the real time basis, the two dimensional position of any defects as reflected on the end face of the partition wall can readily be identified. Thus, those particles originating from a defect in the module may be readily discriminated by the eyes from those not originating therefrom, because scattering of the light rays occurs repeatedly and relatively regularly for a particular defective point when the particles are originating from a defect. By analogy, the irradiated particles originating from a defect look like a series of air bubbles arising consecutively from a nozzle in water, whereas the behavior of secondary particles not directly deriving from the defect is quite random.

Use of airborne fine particles or dusts and visualization thereof by scattered light rays are particularly effective in detecting extremely small defects and in precisely identifying the location of the defects.

The intensity of the scattered light rays is very weak since the particles are extremely fine and generally have a submicron particle size in the order of a fraction of a micrometer. In view of this, it is preferable to intensify the scene of the scattered light rays by an image intensifier. The intensified image may be presented for visual inspection by an operator to determine the position of the defect. Alternatively, the intensified image may further be input into a conventional video camera for display on a video monitor to enable the operator to inspect and work on an enlarged screen. As another alternative, the video signals from the video camera may be forwarded to a data processor for statistically determining the two dimensional position of the defect. The resulting data indicating the two dimensional position of the defect may be displayed on a video monitor to enable the operator to mark the defects on the end face of the module or may be transferred to an XY table for use in repair purposes.

These features of the invention as well as other features and advantages thereof will become apparent from the following description made in conjunction with the accompanying drawings.

DESCRIPTION OF THE PREFERRED EMBODIMENTS

By way of example, the preferred embodiments of the invention will be described with reference to the drawings.

Figure 1:
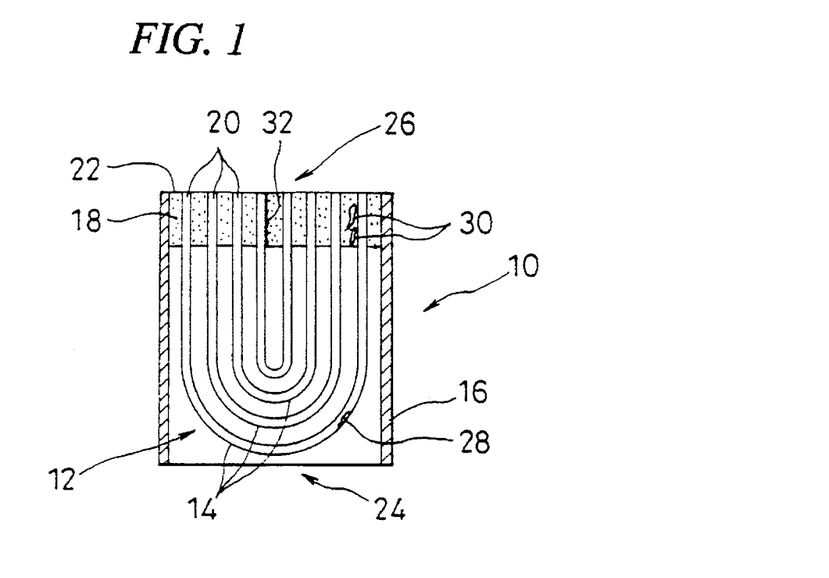
FIG. 1 is a schematic cross-sectional representation of a typical hollow fiber membrane module, showing various defects to be detected.

Referring first to FIG. 1 wherein an example of the conventional hollow fiber membrane module is schematically shown, the module 10 includes a bundle 12 of microporous hollow fibers 14 numbering, for example, from several tens to ten thousands. As is well-known, the tubular wall defining each of the hollow fibers 14 serves as a filtration membrane and is therefore provided with micropores, not shown, the size of which may vary from ten micrometers to a fraction of a micrometer depending on the intended purpose of the module. For example, high quality modules used for purification of water normally have a submicron pore size in the order of a fraction of a micrometer. Typically, the hollow fibers 14 are arranged in a tubular casing 16 in such a manner that the ends thereof are sealingly supported by a partition wall 18 of potting resin bonded to the casing, with the inner channels 20 of respective fibers 14 being open onto the outer end face 22 of the partition wall. In use, a fluid to be filtered or processed is applied to the unfiltered side 24 of the module and is allowed to flow through the membrane wall into the inner channels 20 of respective fibers 14 so that the filtered fluid is collected at the filtered side 26.

As described, for example, in Japanese Patent Kokai Publication No. 3-169329, the module may be manufactured by inserting the bundle 12 into the casing 16, by injecting a quantity of uncured potting material such as polyurethane resin at an end of the casing 16 by the conventional molding process, and by cutting the product along a cutting plane to form the end face 22. The module 10 as manufactured may be defective due to the presence of pinholes or fissures 28 appearing in any of the fibers 14, voids or cavities 30 formed in the partition wall 18 during molding thereof, or cracks or splits 32 resulting from inadequate bonding between the fibers and the partition wall. The two dimensional position of these defects as reflected on the end face 22 are detected according to the invention and the defective modules are subjected to repair and mending.

Figure 2:
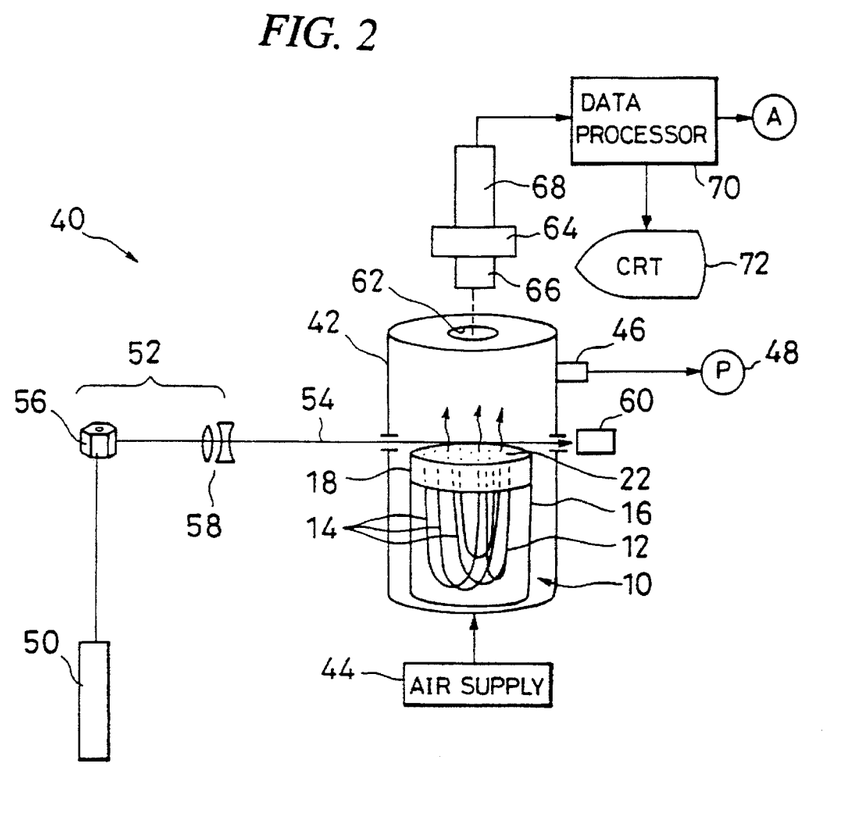
FIG. 2 is a schematic view of the detecting apparatus according to the first embodiment of the invention, with the image intensifier and video camera being shown as dismounted from the dark enclosure.

Referring now to FIG. 2 wherein the apparatus 40 for detecting the two dimensional position of a defect according to the first embodiment of the invention is shown, the arrangement and the mode of operation thereof as well as the method according to the invention will be described. The apparatus 40 includes a dark chamber 42 adapted to receive the hollow fiber membrane module 10 which may be suitably fixed on the bottom wall of the chamber. The bottom wall of the chamber has an air inlet connected preferably to an air supply system 44 which is adapted to supply dry air carrying airborne particles of a predetermined known particle size. A suitable example of the air supply system 44 is the testing air supply system KG-05 marketed by Rion K.K. of Tokyo, Japan, which is designed to provide dried air wherein particles of polystyrene latex of a selected size are uniformly suspended. The size of the particles may be selected to be larger than the effective pore size of the micropores of the module to be tested. In the case of the module having an effective pore size of about 0.1 micrometer or less, the use of particles having a particle size of about 0.2–0.3 micrometers is preferable. Although the use of polystyrene latex particles having selected known particle size is preferable, this is not mandatory. Thus, for the purpose of the present invention, ambient air carrying airborne dusts of varying indeterminate particle size may well be used as a source of airborne particles.

The outlet 46 of the chamber is connected to a vacuum-pump 48 to draw air across the module 10 as shown by the arrows to cause the airborne particles to pass through any defects in the module. Alternatively, air from the supply system 44 may be pressurized to force it to flow through the module. The preferable flow rate of air is from 0.1 to 1 m/sec.

The apparatus 40 also includes a source of beam of light rays, such as a laser 50, and an optical system 52 for projecting the laser beam 54 along a plane parallel to and closely adjacent to the end face 22 of the module 10 in the chamber 42 to irradiate and visualize by the scattered light rays the particles that have passed the defects, if any, in the module 10. Generally, the intensity of light as scattered by a particle is proportional to the sixth power of the particle size but is inverse proportional to the fourth power of the wave length of the incident light. In view of the extremely small size of the particles, it is therefore desirable that the wave length of the laser beam be as short as possible in order to obtain scattered light of adequately high intensity. To this end, it is preferable to use an argon laser which is capable of generating a laser beam having a wave length of from 351 to 514 nanometers and which has an output power ranging from about 10 mW to 20 W.

Figure 3:
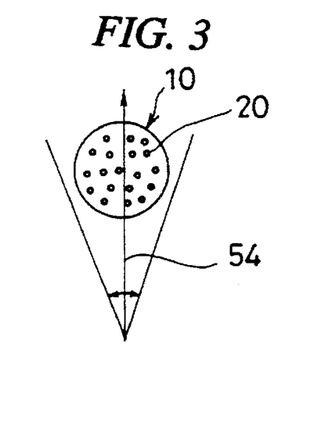
FIG. 3 is a schematic top plan view showing the laser beam as scanned over the end face of the module in the apparatus of FIG. 1.

In the illustrated embodiment, the optical system 52 includes a polygonal mirror 56, rotated by an electric motor, not shown, and a collimator lens system 58 which are arranged to cyclically scan the laser beam 54 over the end face 22 of the module as shown in FIG. 3. As the scanning laser beam impinges upon the particles issuing from the defects in the module, the particles will scatter the incident beam to present a scene wherein the particles are visualized by the spots of scattered light rays. The remaining laser beam is trapped and attenuated by a beam block 60.

In order to precisely identify the position of the defects, and in order to avoid formation of the spots of scattered light resulting from airborne particles that are not directly originating from the defects, it is desirable that the plane in which the laser beam is projected is as close to the end face 22 of the module 10 as possible. It will be noted, however, that, if the laser beam were projected too close to the end face 22 of the module, the end face 22 would unnecessarily be illuminated so that the light intensity of the background underlying the scene of the scattered light rays will be increased. This is undesirable because the contrast of the scene of the scattered light vis-a-vis the background thereof is diminished thereby making it difficult to highlight the particles. For these reasons, it is preferable that the plane of projection of the laser beam be spaced for a small distance in the order of 10 mm away from the end face 22.

The scene of the scattered light rays as generated by the irradiated particles may be visually observed and inspected directly by an operator through a view window 62 provided on the top wall of the dark chamber 42, for identification of the two dimensional position of the defects. According to the preferred embodiment illustrated, however, the apparatus 40 is designed such that the light intensity of the scene is magnified to produce an intensified image which is then converted into video signals for subsequent image processing. To this end, an image intensifier 64 with an objective 66 is snugly and tightly mounted on the top wall of the chamber 42 to view the scene of scattered light rays developed in the dark chamber. A preferred example of the image intensifier 64 is the high sensitivity image intensifier V2025 available from Hamamatsu Photonics K.K. of Shizuoka, Japan. This image intensifier includes an electronic lens which intensifies the incident light rays to focus the intensified image on a fluorescent screen thereof.

The intensified image thus focused on the screen of the image intensifier is viewed by a conventional video camera 68 of the type having an area image sensor comprised of charge coupled device (CCD), which delivers in the conventional manner analog video signals that correspond to the intensified image. It will be noted, however, that the intensified image may be presented as such for the inspection by the operator for determination of the two dimensional position of the defects. In the illustrated embodiment, the arrangement is such that the video signals obtained by the video camera 68 is forwarded to a data processor 70 for image processing described later with reference to FIGS. 6 and 7. Otherwise, the video signals may be supplied without processing to a conventional video monitor 72 for displaying the intensified image on the real time basis to permit operator's inspection.

The data processor 70 may comprise a conventional general purpose digital computer wherein a conventional image processing kit available on the market is suitably equipped and loaded. The present inventor has successfully used an IBM compatible general purpose personal digital computer to which is mounted and installed the general-purpose high-speed image processing kit marketed by Ezel Sharp Semiconductor Inc. of Tokyo, Japan. The kit includes a first circuit board "GPB-1" for image processing and memory and a second circuit board "INCARD" for analog to digital (A/D) conversion of video signals. These circuit boards are adapted to be mounted to an IBM compatible computer by simple insertion. The kit also includes a "GUI" software package for operating the GPB-1. Those skilled in the art may readily implement the software by installing it on a hard disc of the computer.

Figure 4:
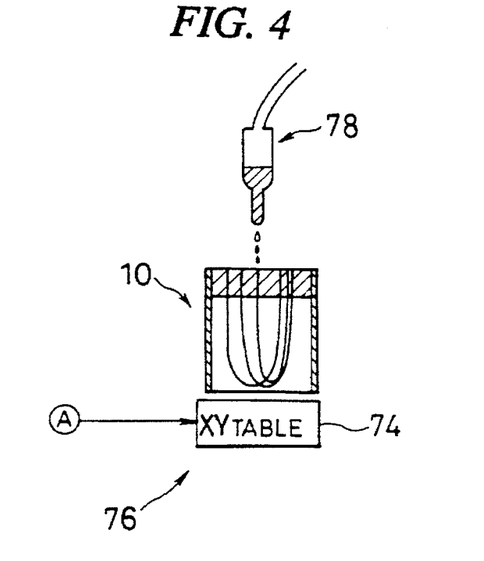
FIG. 4 is a schematic view showing a repair station.
Figure 5A:
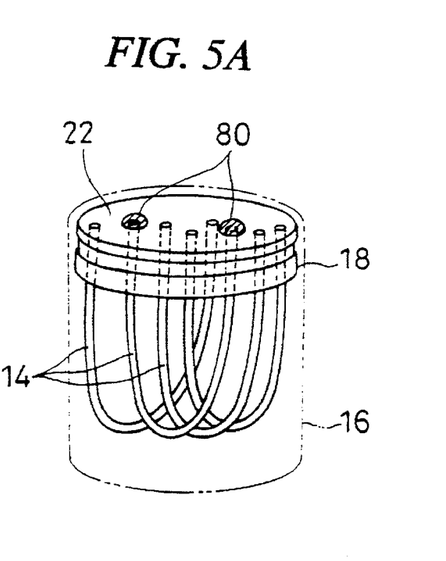
FIGS. 5A and 5B are schematic perspective and cross-sectional views, respectively, showing the defective module after repair.
Figure 5B:
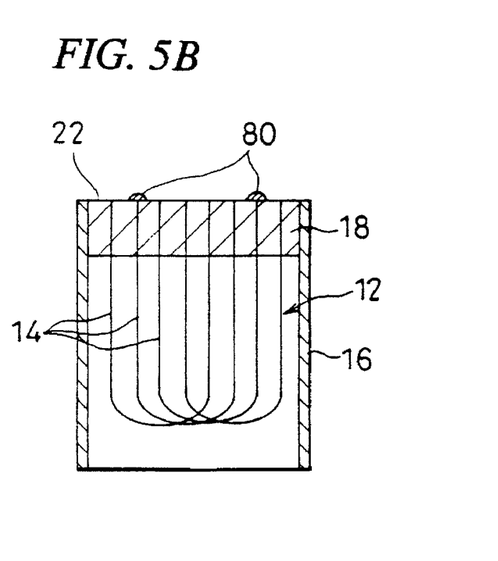

As described later, the data processor 70 processes the video signals from the video camera 68 to provide an information on the two dimensional position of any defects in the module 10. The two dimensional information is displayed on the video monitor 72 and is also forwarded to an XY table 74 of a repair station 76 shown in FIG. 4. The repair station 76 may include a fixed injection nozzle 78 adapted to dispense a metered quantity of uncured sealing agent such as potting resin. The defective module 10 is placed on the XY table 74 in a proper orientation based on a suitable reference mark affixed to the module. The XY table is then operated to bring each of the defective portions of the module successively below the injection nozzle 78. The nozzle 78 is activated in synchronization with the XY table 74 to apply a quantity of sealing agent 80 on the end face 22 of the module as shown in FIGS. 5A and 5B at each point where a defect is reflected. For example, when a particular hollow fiber is defective due to the presence of a pinhole or fissure 28 (FIG. 1), the particles will appear at both open ends of the inner channel 20 of that particular fiber so that the testing and detecting apparatus 40 will identify that the module is defective at two points. Accordingly, both open ends of the inner channel 20 of the particular fiber are sealed as shown in FIGS. 5A and 5B. When the partition wall 18 is defective for the presence of cavity 30 or crack 32, it will suffice to seal the end face at a single location. In any case, the sealing agent may be applied to cover a sufficient surface area surrounding the defective position.

Figure 6:
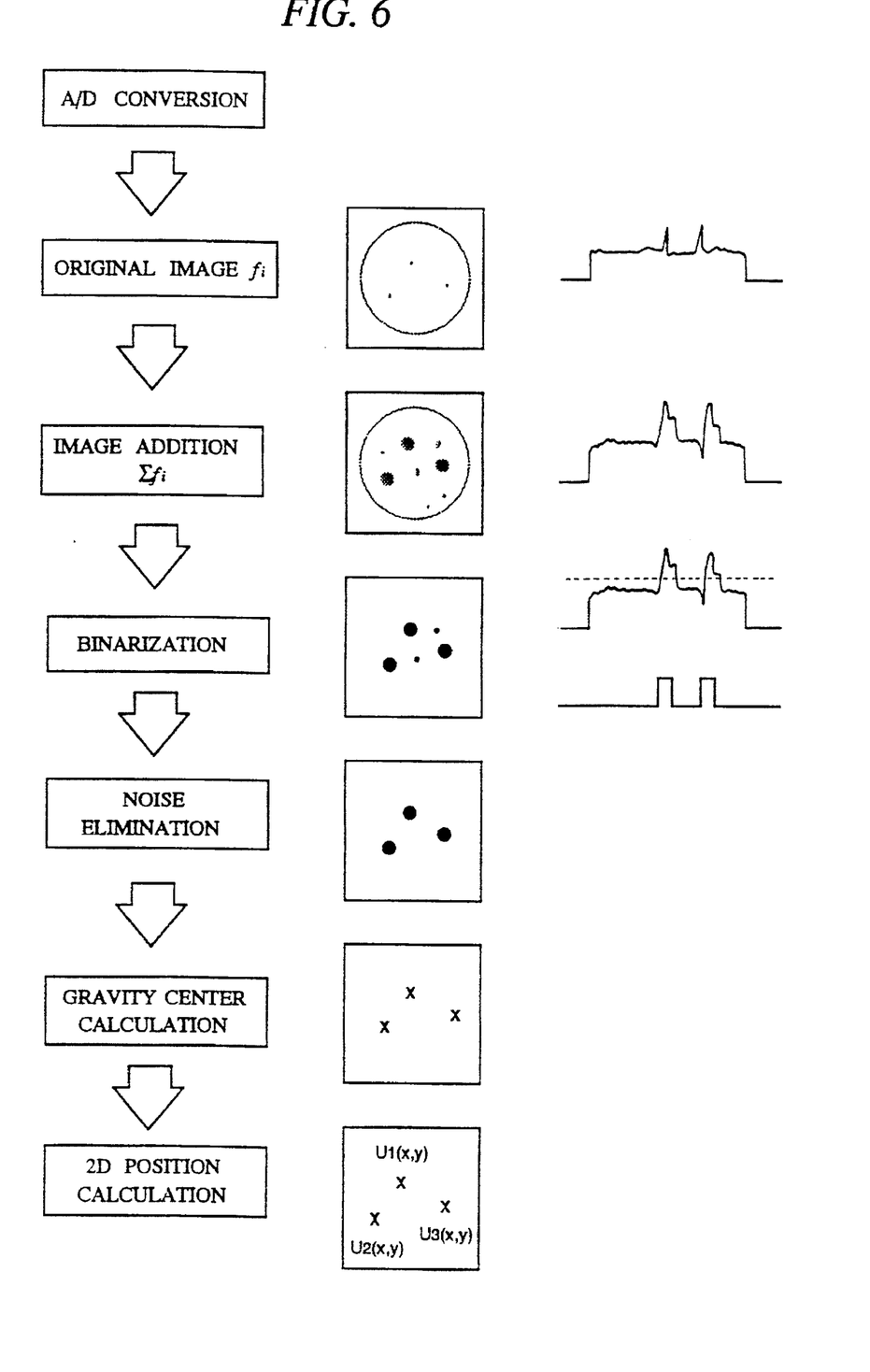
FIG. 6 is a diagram illustrating the mode of image processing, with the left-hand column showing various stages of processing, the central column showing the images obtained at different stages, with the right-hand column showing video signals at a certain stages.

Referring to FIG. 6, the mode of data processing performed by the data processor 70 will be described. In FIG. 6, various stages of processing are shown in the left-hand column, with the central column illustrating the images corresponding to respective stages and with the right-hand column showing video signals at different stages. As is well-known, the conventional video camera 68 generally delivers serial analog video signals at a rate of 30 shots per second, with each shot forming an image comprising 525 horizontal scanning lines. The analog video signals are converted into binary digital signals wherein the light intensity of each picture element in the image is represented by one of 256 tones, for example. In the original image fi corresponding to one shot, the spots of scattered light rays developed by the particles passed any defects will appear as shown in the second column of FIG. 6. An example of digital video signals pertaining to a single scanning line is shown in the right-hand column of FIG. 6.

Then, the original images taken during 5 seconds of testing (150 shots), for example, are summed to produce an added image $\Sigma fi$, by summing the digital data for each picture element in the image. In the added image $\Sigma fi$, a spot of scattered light rays originating from a particular defect will appear as consisting of a set of adjacent picture elements as shown in the central column of FIG. 6. The summed digital signals pertaining to a single scanning line are shown in FIG. 6 to the right of the added image.

Thereafter, the added video signals are subjected to binarization whereby the summed video signals are compared with a given discrimination level and are converted into two-valued signals, as shown in the right-hand column of FIG. 6. The resulting binarized signals are then subjected to noise elimination to remove any unnecessary noise signals related to isolated points which consist of a set of limited number of picture elements and which, therefore, do not properly reflect the defect. The illuminated spots remaining in the image after noise elimination will represent the position of the defects in the module with a high degree of reliability. Then, the center of gravity is calculated for each of the illuminated spots and the two dimensional position in the XY coordinate is calculated for each defect. The data representing the two dimensional position of the defects are delivered to the XY table 74 and the video monitor 72 as described before.

Figure 7:
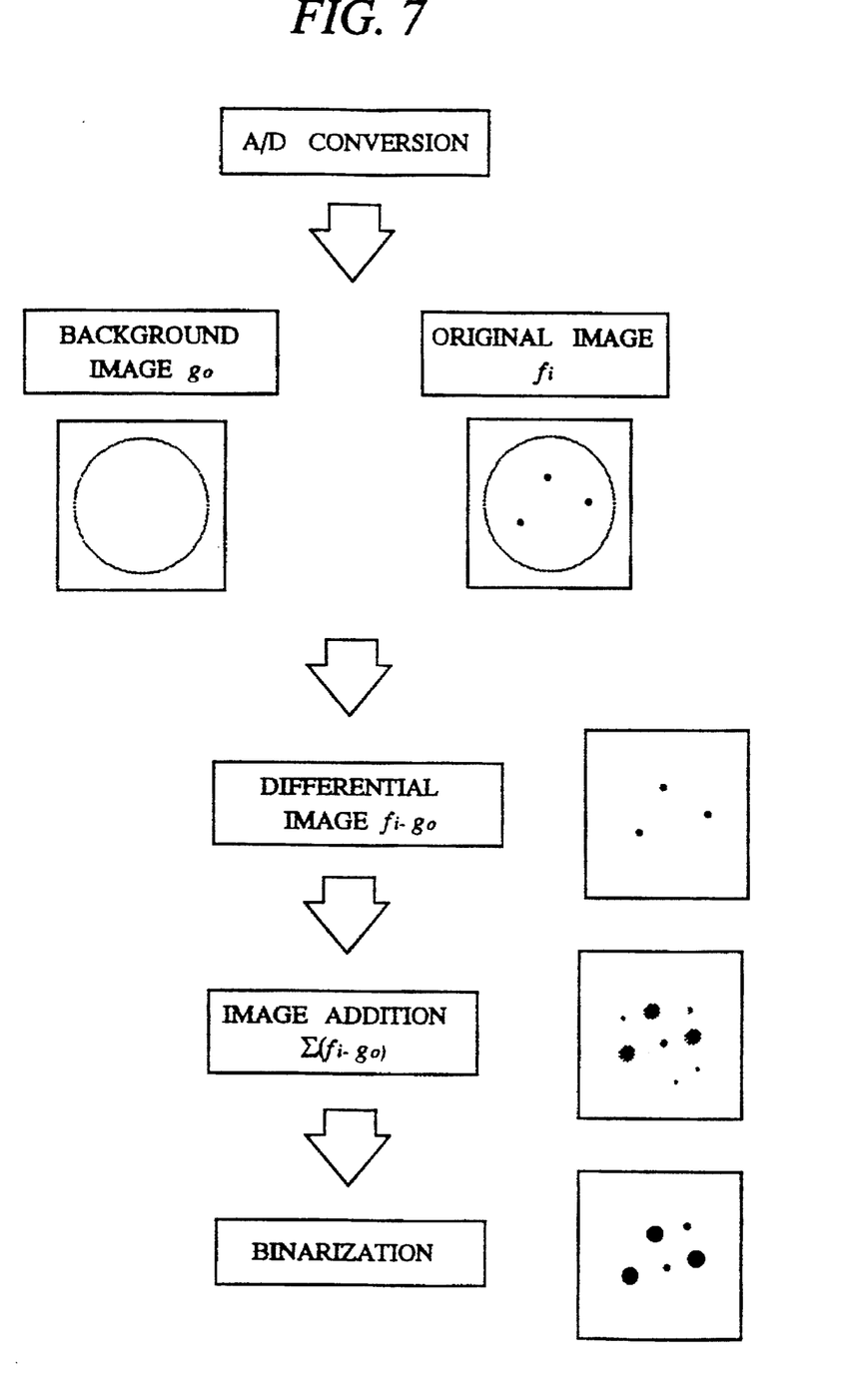
FIG. 7 is a diagram similar to FIG. 6 but showing an alternative mode of image processing.

FIG. 7 illustrates an alternative mode of image processing. In this mode, the analog video signals from the video camera 68 is analog-to-digital converted prior to operation of the vacuum pump 48 to derive digital video signals showing the background image go in which may appear the circular configuration of the module as as well as any regions of the end face 22 of the module that are illuminated. As the vacuum pump 48 is operated to draw particles through defects in the module, the digital video signals showing the original image fi of the scattered light rays are derived and the background image go is subtracted from the original image fi to form a differential image fi-go. Then, the differential images are summed for a predetermined number of shots to produce an added differential image $\Sigma(fi-go)$, which is thereafter subjected to binarization and subsequent processing in the manner similar to that described with reference to FIG. 6. This mode is advantageous in that the added image is more free from noise signals because the background image which would affect the quality of the added image has been removed preliminarily.

Figure 8:
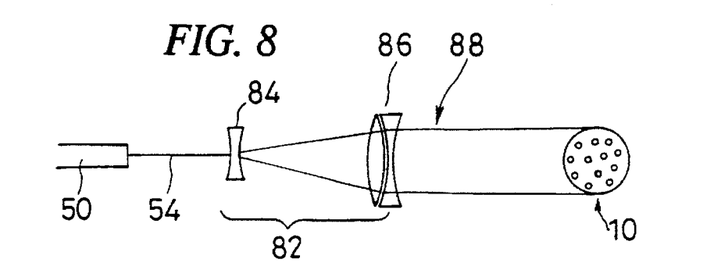
FIG. 8 is a schematic top plan view showing a modified form of the optical system shown in FIG. 2.

FIG. 8 illustrates a modified form of the optical system 52 shown in FIG. 2. In the modified arrangement 82, the laser 50 is aligned with a cylindrical lens 84, a collimator lens assembly 86 and the module 10. The laser beam 54 from the laser 50 is horizontally diverged by the cylindrical concave lens 84 and is then collimated by the collimator 86 in the horizontal direction as well as in the vertical direction to form a horizontally spread, collimated slit-light 88 which is then projected along the plane closely adjacent to the end face 22 of the module 10 to be tested. The scene of the scattered light rays are imaged and processed in a manner similar to that described with reference to the foregoing embodiment. The modified arrangement advantageously permits to detect the defects more quickly because the particles originating from the defects are irradiated whenever they traverse the plane of the slit-light. Moreover, the detecting apparatus 40 can be made simple in structure since the scanning mirror system is not required.

Figure 9:
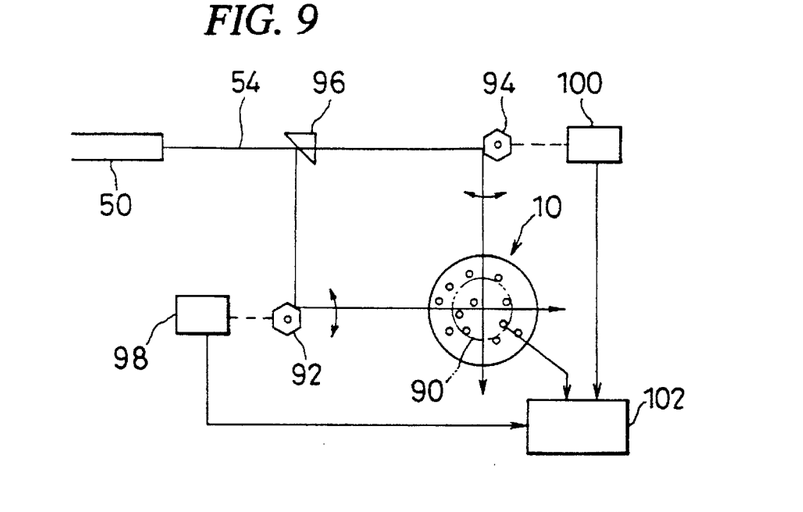
FIG. 9 is a schematic top plan view showing another embodiment of the invention; and, FIG. 10 is a block diagram of the detecting circuit shown in FIG. 9.
Figure 10:
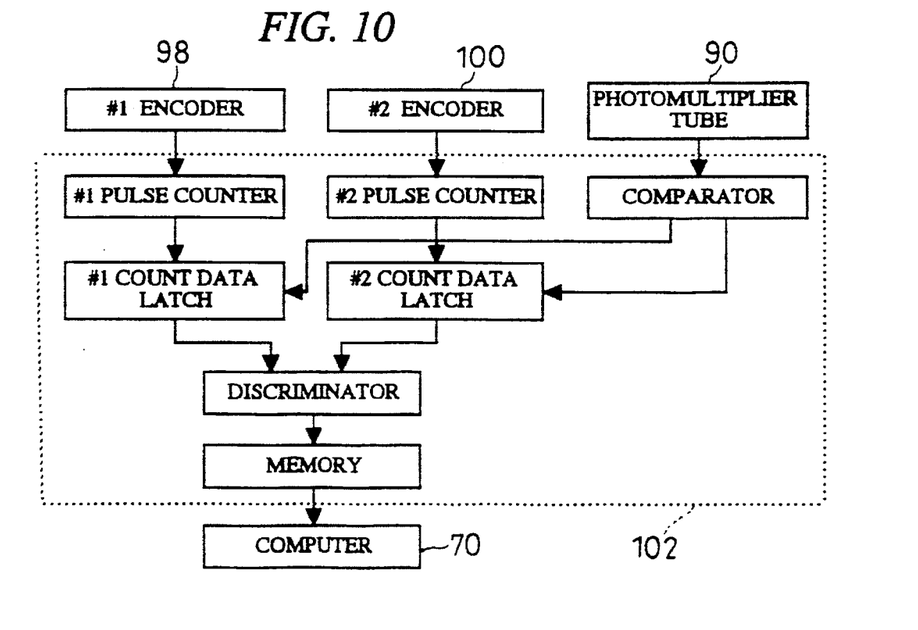

FIGS. 9 and 10 illustrate another embodiment of the invention. Briefly, the feature of this embodiment is that, in place of the combination of the image intensifier 64 and the video camera 68 as used in the embodiment shown and described with reference to FIG. 2, a photosensitive device such as a photomultiplier tube 90 is used which is adapted to simply detect the presence or absence of the scattered light rays. As the photomultiplier tube 90 is unable to detect the two dimensional position of the spot of scattered light rays, the optical system is designed to scan the laser beam in the X and Y directions.

Referring to FIG. 9, the optical system includes first and second polygonal mirrors 92 and 94 rotated by electric motors, not shown. The laser beam 54 from the laser 50 is bifurcated by a half mirror 96 and is simultaneously directed to the first and second mirrors. The mirrors 92 and 94 are timed such that the laser beam is alternately scanned above the end face 22 of the module 10 to be tested. The polygonal mirrors 92 and 94 are connected, respectively, to first and second rotary encoders 98 and 100 of the conventional type which deliver pulse signals to a detecting circuit 102 in response to the rotation of the associated mirrors. Similar to the first embodiment shown in FIG. 2, air carrying sized polystyrene particles is forced to flow through the module 10 in the dark chamber and the scattered light rays are detected by the photomultiplier tube 90 mounted to the top wall of the dark chamber 42.

The mode of operation of this embodiment will be described with reference to FIG. 10. The output pulse signals from the first and second rotary encoders 98 and 100 are forwarded, respectively, to first and second pulse counters of the detecting circuits 102 for counting the number of pulses generated as the polygonal mirrors 92 and 94 have been rotated from an initial angular position. The count data are sent to associated latching circuits. The photomultiplier tube 90 senses the scattered light rays when the laser beam either from the first or second polygonal mirror 92 or 94 illuminates a particle which has passed a defect in the module 10. Upon sensing the scattered light, the photomultiplier tube 90 delivers a signal which is applied to a comparator. The comparator compares the level of the output signal with a threshold level and, if the signal from the photomultiplier tube 90 is higher than the threshold, then triggers the latching circuits to hold the count data. The data of pulse count are supplied to a discriminator which operates to check the angular position of the first and second mirrors 92 and 94 and to determine which one of the mirrors is now projecting the laser beam. Then, the discriminator sends the pulse count data to a memory to cause it memorized. Each time scanning of the laser beam is completed by either of the mirrors 92 and 94, the data processor 70 accesses the memory and retrieves the memorized data. Then, the data processor 70 computes the angle of the laser beam at the moment where the scattered light rays are sensed and calculates the position of the defect in the XY coordinate. The obtained data may be displayed on the video monitor 72 and forwarded to the XY table 74 in the similar manner as the first embodiment.

While the present invention has been described herein with reference to the specific embodiments thereof, it is contemplated that the invention is not limited thereby and various modifications and alterations may be made therein without departing from the scope of the invention. For example, instead of using the video camera 68, detection of the two dimensional position of a defect may be carried out by a semiconductor position sensitive detector.

I claim:

1. An apparatus for testing a hollow-fiber-membrane module for the presence or absence of a defect and for detecting, in the presence of a defect, a two dimensional position thereof, said module including a plurality of microporous hollow fibers having at least one end thereof sealingly bonded to and supported by a partition wall with the inner channels thereof opening onto an end face of said partition wall, said apparatus comprising:

- a substantially dust-free dark enclosure adapted to accommodate the module;
- a source of gaseous fluid carrying fine particles having a particle size larger than the effective pore size of the micropores of said hollow fibers;
- means for forcing said fluid to flow through the module from unfiltered to filtered sides thereof to cause, in the presence of a defect, said particles to pass through said defect downstream of said end face;
- optical means for projecting light rays along a plane parallel to and closely adjacent to said end face of the module in said enclosure to irradiate said particles as they traverse said plane to cause said particles to be visualized by light rays scattered thereby;
- an image intensifier arranged opposite said end face for generating an intensified image of visualized particles;
- a video camera associated with said image intensifier for generating video signals corresponding to said intensified image; and,
- a video monitor responsive to said video signals to display on the real time basis an image of the light scattering particles to enable an operator to visually identify the two dimensional position of said defect as reflected on said end face.

2. An apparatus for testing a hollow-fiber-membrane module for the presence or absence of a defect and for detecting, in the presence of a defect, a two dimensional position thereof, said module including a plurality of microporous hollow fibers having at least one end thereof sealingly bonded to and supported by a partition wall with the inner channels thereof opening onto an end face of said partition wall, said apparatus comprising:

- a substantially dust-free dark enclosure adapted to accommodate the module;
- a source of gaseous fluid carrying fine particles having a particle size larger than the effective pore size of the micropores of said hollow fibers;
- means for forcing said fluid to flow through the module from unfiltered to filtered sides thereof to cause, in the presence of a defect, said particles to pass through said defect downstream of said end face;
- optical means for projecting light rays along a plane parallel to and closely adjacent to said end face of the module in said enclosure to irradiate said particles as they traverse said plane to cause said particles to be visualized by light rays scattered thereby;
- an image intensifier arranged opposite said end face for generating an intensified image of visualized particles;
- a video camera associated with said image intensifier for generating first video signals corresponding to said intensified image;
- image processor means for processing said first video signals to provide second video signals representing an image of scattered light rays having a predetermined number of occurrence; and,
- a video monitor responsive to said second video signals to display the two dimensional position of said defect as reflected on said end face.

3. An apparatus for testing a hollow-fiber-membrane module for the presence or absence of a defect and for detecting, in the presence of a defect, a two dimensional position thereof, said module including a plurality of microporous hollow fibers having at least one end thereof sealingly bonded to and supported by a partition wall with the inner channels thereof opening onto an end face of said partition wall, said apparatus comprising:

- a substantially dust-free dark enclosure adapted to accommodate the module;
- a source of gaseous fluid carrying fine particles having a particle size larger than the effective pore size of the micropores of said hollow fibers;
- means for forcing said fluid to flow through the module from unfiltered to filtered sides thereof to cause, in the presence of a defect, said particles to pass through said defect downstream of said end face;
- a source of light rays;
- optical means for projecting the light rays along a plane parallel to and closely adjacent to said end face of the module in said enclosure to irradiate said particles as they traverse said plane to cause said particles to be visualized by light rays scattered thereby;
- an image intensifier arranged opposite said end face for generating an intensified image of visualized particles;
- a video camera associated with said image intensifier for generating video signals corresponding to said intensified image; and,
- image processor means for processing said video signals to derive an information on the two dimensional position of said defect as reflected on said end face.

4. An apparatus according to claim 3, wherein said source of light rays is a laser.

5. An apparatus for testing a hollow-fiber-membrane module for the presence or absence of a defect and for detecting, in the presence of a defect, a two dimensional position thereof, said module including a plurality of microporous hollow fibers having at least one end thereof sealingly bonded to and supported by a partition wall with the inner channels thereof opening onto an end face of said partition wall, said apparatus comprising:

- a substantially dust-free dark enclosure adapted to accommodate the module;
- a source of gaseous fluid carrying fine particles having a particle size larger than the effective pore size of the micropores of said hollow fibers;
- means for forcing said fluid to flow through the module from unfiltered to filtered sides thereof to cause, in the presence of a defect, said particles to pass through said defect downstream of said end face;
- a source of beam of light rays;
- scanning means for scanning said beam along a plane parallel to and closely adjacent to said end face of the module in said enclosure to irradiate said particles as they traverse said plane to cause said particles to scatter the incident beam, said scanning means including a first scanning mirror for scanning said beam about a first direction and a second scanning mirror for scanning said beam about a second direction perpendicular to said first direction;
- rotary encoders associated, respectively, with said first and second scanning mirrors for delivering signals indicative of the angular positions of said beam;
- photosensitive means responsive to the light rays scattered by said particles to deliver a signal upon sensing the scattered light rays; and,
- data processing means responsive to said signals from said encoders and said photosensitive means for detecting the two dimensional position of said defect as reflected on said end face.

* * * * *